(12) United States Patent
Goenner et al.

(10) Patent No.: US 6,468,475 B1
(45) Date of Patent: Oct. 22, 2002

(54) AUTOSAMPLER

(75) Inventors: Winfried Goenner, Uberlingen (DE);
Donald L. Groeschner, New Milford;
E. Joel McCorkle, Woodbury, both of CT (US)

(73) Assignee: PerkinElmer Instruments LLC, Shelton, CT (US)

( * ) Notice: Subject to any disclaimer, the term of this patent is extended or adjusted under 35 U.S.C. 154(b) by 0 days.

(21) Appl. No.: 09/518,466

(22) Filed: Mar. 3, 2000

Related U.S. Application Data

(60) Provisional application No. 60/122,992, filed on Mar. 5, 1999.

(51) Int. Cl.$^7$ .......................... G01N 35/02; G01N 35/10
(52) U.S. Cl. ..................... 422/64; 743/864.85; 239/692
(58) Field of Search ........................ 422/64; 73/864.85; 239/692

(56) References Cited

U.S. PATENT DOCUMENTS

| | | | | |
|---|---|---|---|---|
| 2,328,408 A | * | 9/1943 | Kenyon ........................ | 73/809 |
| 4,490,084 A | * | 12/1984 | Collier et al. ............... | 414/222 |
| 5,398,556 A | * | 3/1995 | Lang ........................ | 73/866.11 |

FOREIGN PATENT DOCUMENTS

| | | | | |
|---|---|---|---|---|
| JP | 3-195313 | * | 8/1991 | .................... 414/4 |

* cited by examiner

Primary Examiner—Thomas P. Noland
(74) Attorney, Agent, or Firm—St. Onge Steward Johnston & Reens LLC

(57) ABSTRACT

An autosampler for manipulating a specimen container into and out of a furnace of a parent instrument is disclosed. The autosampler has upper, lower and middle gripping fingers which grip and stabilize a crimped wire, which has a large bend therein. The middle gripping finger is positioned between and opposed to the upper and lower gripping finger and has a portion at one end thereof sized and shaped to receive the bend of the crimped wire. The gripping fingers grip and hold the crimped wire while a tray table moves to place the specimen container on a hook at the bottom of the crimped wire. If the specimen container is sealed, a hole may be punctured therein by a puncturing apparatus, which has a housing which is movable between an upper and lower position and biased toward the lower position. A pin is positioned inside the housing. When the specimen tray moves into the upper position, the sealed specimen container moves the housing from the lower position to the upper position thereby exposing the pin and causing it to puncture the sealed specimen container. An electrostatic discharge device which includes a housing having a channel thereabout is also provided. A high voltage source is electrically connected to a pin positioned inside the housing and in fluid communication with the channel for supply voltage to the pin and generating multiple free ions as a result thereof. Pressurized gas directs the free ions toward an electrostatic field to neutralize the ions therein.

13 Claims, 10 Drawing Sheets

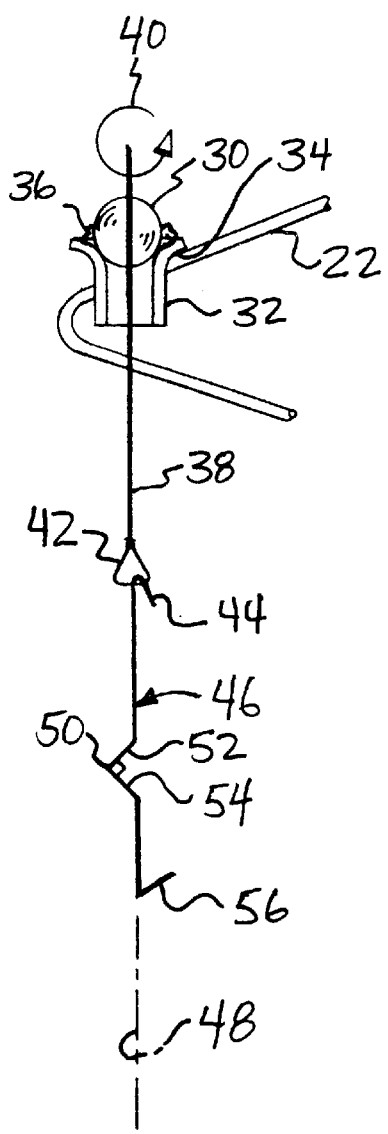
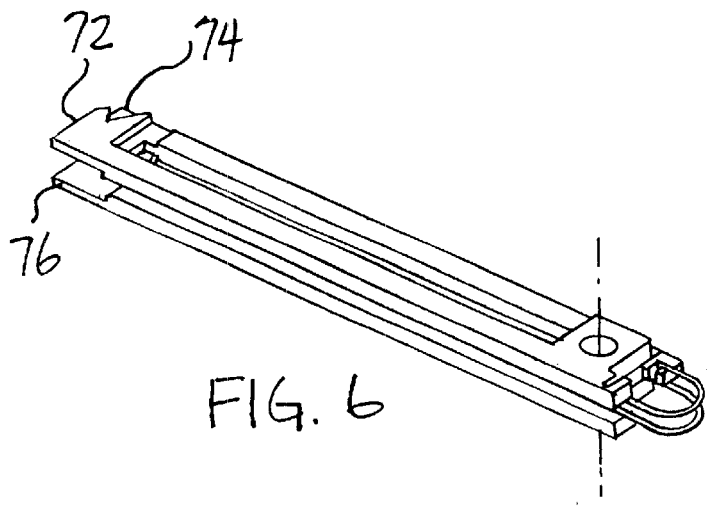
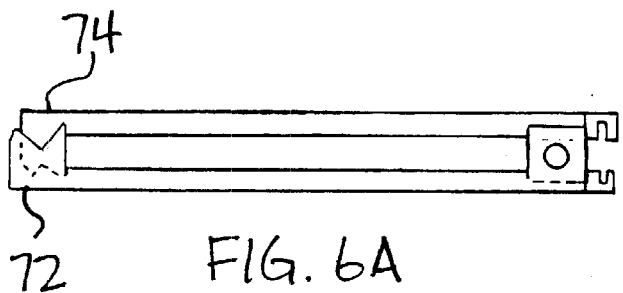
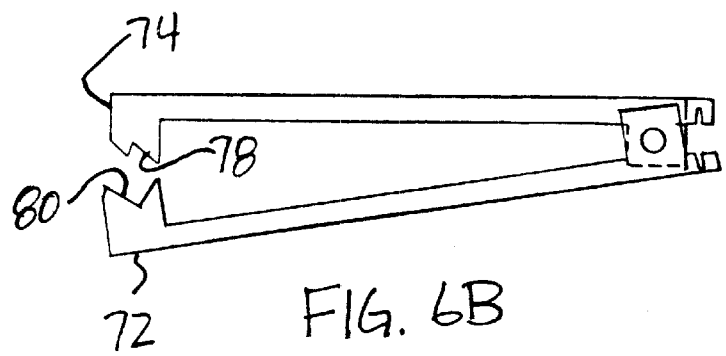
FIG. 5
FIG. 6
FIG. 6A
FIG. 6B

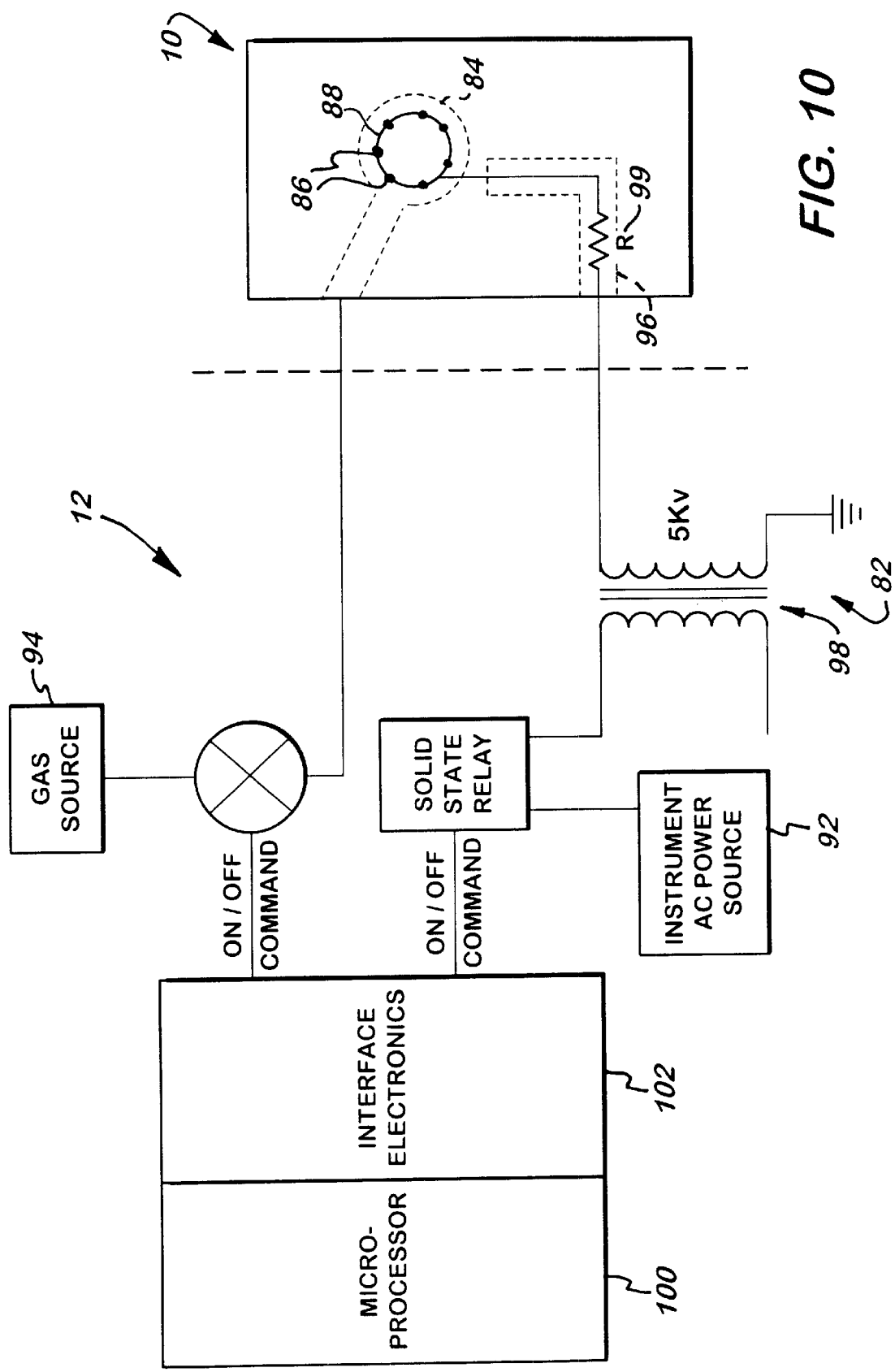

AUTOSAMPLER

CLAIM OF PRIORITY

This application claims the benefit of from U.S. Provisional Patent Application No. 60/122,992 filed Mar. 5, 1999.

FIELD OF THE INVENTION

The present invention relates to an automatic sampling device and, in particular, to a device that automatically transfers a sample container from a sample tray to known laboratory analyzing equipment, for the examination of, for example, the heats of transformation of a sample, and which transfers the sample container from the analyzing equipment to the sample tray.

BACKGROUND OF THE INVENTION

It is known to use thermal gravimetric analysis (TGA) systems to conduct thermal analyses of selected samples, also referred to herein as specimens, in order to examine certain characteristics of the samples as a function of temperature. As it is sometimes necessary to carry out measurements on a large number of samples, it is desirable and known in the art to mechanize the manipulation of the specimens. Such mechanization is commonly referred to as autosampling.

One autosampler is shown in U.S. Pat. No. 5,398,556 to Lang. Lang discloses a device having a vertical gripper member and a rotatable specimen plate for holding a plurality of specimen containers. A specimen container is transferred to the measuring location in the parent machine (e.g., a TGA) by rotating the specimen plate so that the desired specimen container is positioned under the gripper. Then, the gripper, which is driven by a motor, is lowered and gripping fingers attached to a gripping member grip the specimen container. The container is then raised from the specimen plate by raising the gripping member. The specimen plated is then rotated until a recess in the specimen plate is located underneath the gripping member. Next, the gripping member is lowered through the recess in the specimen plate and the specimen container is placed at the measuring location, which is directly underneath the gripper. The specimen container is then deposited on the measuring location by releasing the gripper fingers.

A disadvantage of the gripper taught by the Lang patent is that the device is relatively complicated in that it has many moving parts and that if the motor over- or under-drives the gripper, an error could occur in the placement of the sample.

In conventional thermogravimetric analysis machines, samples are placed in a crucible or sample container that is positioned in a furnace on a platinum ribbon attached to an automatic recording balance. Conventional TGAs are disadvantageous because the platinum wire is easily bent with even a very small force by the gripper when it moves the crucible on and off the balance. After the platinum wire is bent, it is virtually impossible to move back into its original position. If the device is used with a bent wire, it is extremely difficult to accurately position the crucible within the furnace. Further, the act of replacing the platinum wire typically decreases the sensitivity of the machine and detrimentally effects its performance.

Known autosamplers are also disadvantageous because static electricity may accumulate in the furnace area. This is frequently a serious problem which detrimentally effects analytical results. The static buildup generally occurs on the surface of the glassware surrounding the TGA furnace and is aggravated by movement of the glassware over insulating material, such as an O-ring. The resulting electrostatic fields attract the sample container to the surface of the glassware, thus moving the sample container off balance and jeopardizing the advancement of the analysis. Additionally, static electricity may pull some of the sample from the sample pan if the sample pan contains some dust-like particles.

Devices and methods are known to reduce or eliminate static electricity. For example, there are solutions which may be wiped onto glass surface areas. Unfortunately, these known solutions may leave behind a residue which can undesirably build-up on the glass and adversely effect the test results. Alternately, an operator may point a hand-held ion generating device at the area. However, such is undesirable because it requires the operator to stay in the vicinity of the autosampler during the course of the sampling, which can be many hours, and, because the static electricity is not visible, the operator may miss the problem area. Additionally, radioactive emitters are available. However, these are disadvantageous because they have strict disposal requirements.

As is known, conventional autosamplers comprise a sample tray table having a plurality of recesses for holding each of the sample containers in place while the analysis is being conducted. Conventional sample tray tables, however, are disadvantageous because they do not facilitate placement of the sample pan into the recess.

Sometimes it is necessary to work with sealed sample containers, such as when the contents of the sample container are volatile. If a sample container is sealed, it is necessary to puncture the top of the sealed container prior to placing it into the furnace. Conventional puncturing devices are disadvantageous, however, because they have several moving parts and are relatively complicated. Further, disadvantageously, it is sometimes necessary to puncture a sample manually before it is loaded into the tray. When this is done, the sample sometimes loses some of its properties before being loaded into the furnace.

What is desired, therefore, is an autosampler which has a gripper assembly that cooperates with a hanging wire, wherein the hanging wire is not easily bent or damaged and wherein the hanging wire may be easily replaced without reducing the sensitivity of the parent instrument, which is operably connected to an electrostatic discharge device, which has a sample tray table with recesses that facilitate placement of the sample container into the recesses, and which is operatively connected to a safe and reliable puncturing device.

SUMMARY OF THE INVENTION

Accordingly, it is an object of the present invention to provide an autosampler which has a gripper assembly that cooperates with a hanging wire which is durable and not easily damaged.

It is another object of the present invention to provide an autosampler which cooperates with a hanging wire assembly that can be easily replaced without reducing the sensitivity of the parent instrument.

It is still another object of the present invention to provide an autosampler which has a sample tray table with beveled edges and rounded recess areas to facilitate placement of the sample pan into the recesses of the sample tray table.

It is yet a further object of the present invention to provide an autosampler which is operatively connected to an electrostatic discharge device that is safe, effective and easy to use.

It is still another object of the present invention to provide an autosampler which is operatively connected to a puncturing device which has no motorized parts and which is relatively inexpensive to manufacture and simple to construct.

It is still a further object of the present invention to provide an autosampler which is reliable, easy to use, and cost-effective to manufacture and maintain.

To overcome the deficiencies of the prior art and to achieve the objects and advantages listed above, an autosampler is disclosed which comprises a novel gripping assembly which is uniquely sized and shaped to stabilize a crimped wire which hangs from an arm of a balance of the parent instrument. After the gripping assembly grips and stabilizes the wire, a tray table which is positioned about the gripping assembly, moves vertically and rotationally to position a specimen container onto a hook at the bottom of the crimped wire and substantially reverses its steps to remove the container from the crimped wire.

The crimped wire is uniquely designed to be received by the gripping apparatus. The crimped wire has two ends defining an axis therebetween and has at least one point which is displaced from the axis, i.e., the hanging wire is substantially bent at at least one location.

More particularly, the gripper assembly comprises upper, middle and lower gripping fingers, which are movable between an open and a closed position. The upper and lower fingers each have a V-shaped portion at one end for receiving the crimped wire therein and aligning the crimped wire above and below its bend. The middle gripping finger has two ends and is positioned between, and opposed to, the upper and lower gripping finger. The middle gripping finger has a portion at one end thereof sized and shaped to receive the crimped wire at the bend. When the gripping fingers are in the closed position, they grip the crimped wire and stabilize it while the specimen tray moves so as to connect the specimen container to the hook of the crimped wire.

Additionally, the autosampler is operatively connected to an apparatus for puncturing holes into the top of a sealed specimen container. The puncturing apparatus comprises a housing, which is operatively connected to the parent instrument and which is movable between an upper and a lower position. A spring biases the housing into the lower position. A sharp object, such as a pin, is housed inside the housing. When a sealed specimen container is positioned under the sharp object, movement of the tray table to its uppermost position causes the container to force the housing to move from the lower position to the upper position thereby exposing the sharp object. This causes the sharp object to puncture the sealed specimen container.

Additionally, the autosampler is operatively connected to an electrostatic discharge device which reduces or eliminates electrostatic fields which are formed on the surface of glassware of the furnace and on the surface of the autosampler tray and gripper assembly. The electrostatic discharge device comprises a housing which is removably attached to the parent instrument; the housing has a channel thereabout. At least one pin, but preferably a plurality of pins, is positioned inside the housing and in fluid communication with the channel. A source of high voltage alternating current is electrically connected to each pin and supplies voltage to the pins. This generates multiple free ions which cancel the electrostatic field. A source of pressurized gas, such as nitrogen or air, is operatively connected to the housing and forces gas through the channel and around the pins and directs the free ions toward an electrostatic field to neutralize the ions therein.

The invention and its particular features and advantages will become more apparent from the following detailed description when considered with reference to the accompanying drawings.

BRIEF DESCRIPTION OF THE DRAWINGS

FIG. 5 is a side plan view of the hanging wire assembly;

FIG. 6 is an isometric view of the gripper assembly in the closed position;

FIG. 6A is a top view of the gripper assembly of FIG. 6;

FIG. 6B is a top view of the gripper assembly of FIG. 6 shown in the open position;

FIG. 10 is a schematic diagram of electrostatic discharge device shown in FIG. 7;

DETAILED DESCRIPTION OF THE INVENTION

Figure 1:
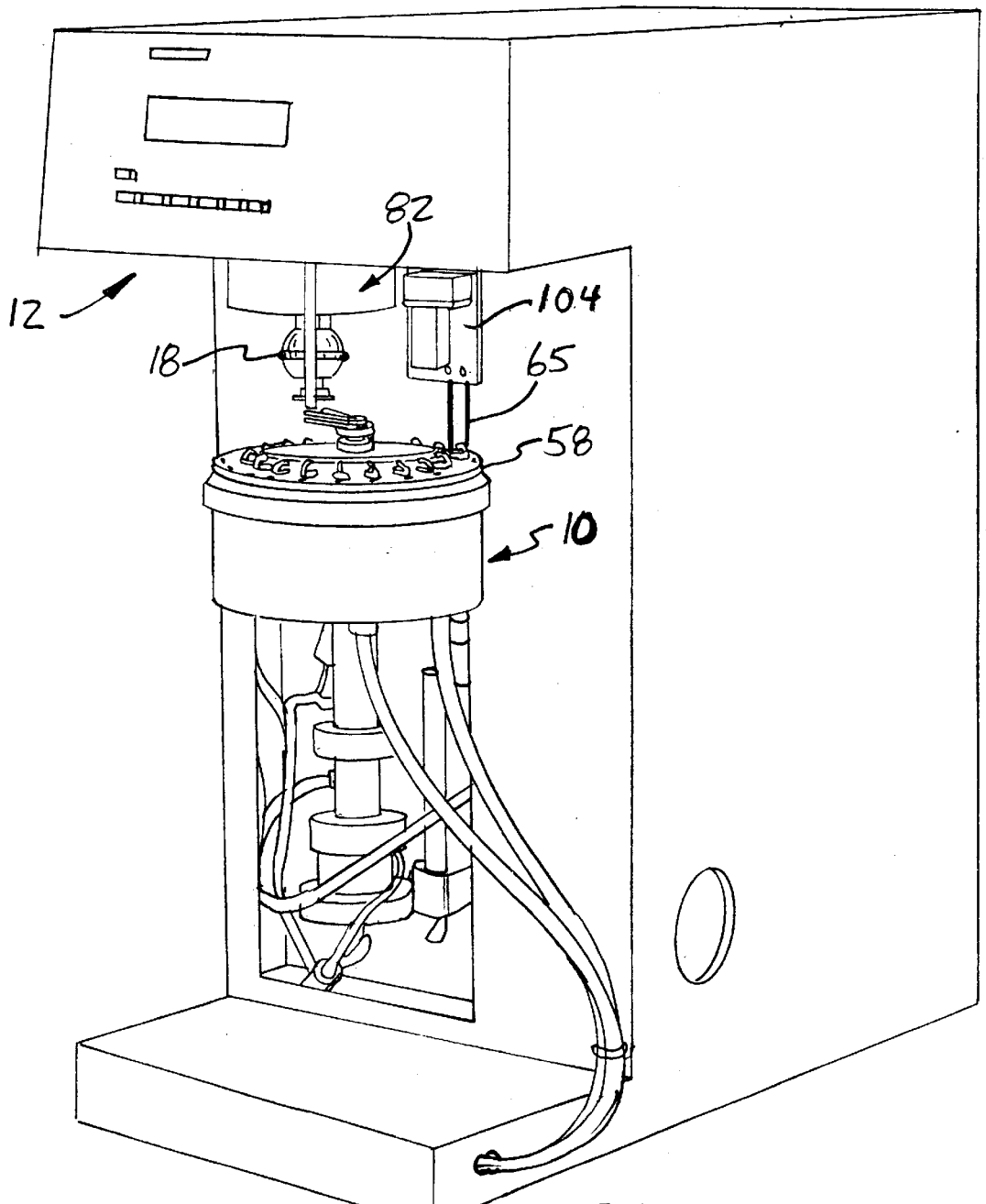
FIG. 1 is an isometric view of an autosampler, constructed in accordance with the present invention.

Referring to the drawings in detail, an autosampler is shown and generally designated by the reference numeral 10. It should be noted that for the sake of clarity not all of the components and parts of auto sampler 10 may be shown and/or marked in all the drawings. As used in this description, the terms "up", "down", "top", "bottom", etc., refer to autosampler 10 when in the orientation illustrated in FIG. 1.

Referring now more particularly to FIG. 1, autosampler 10 is designed to be used with, and operatively connected to, a parent instrument 12, for example, a thermal gravimetric analysis (TGA) machine. As is known, TGA machines conduct thermal analyses of selected samples in order to examine certain characteristics of the samples as a function of temperature. It should be understood that autosampler 10 may be used with other analytical instruments known in the art, after obvious modifications that will become apparent after reading this description. Discussion herein has been limited to the TGA for convenience only and is not intended to be limiting.

Before operations begin, operational data can be provided to a computer (not shown) of the autosampler 10 by an operator through a keyboard (not shown) with a display means (not shown), all of which are known in the art. Alternatively, the computer of the autosampler 10 may be driven by a computer program provided by a host computer (not shown), such as the one marketed by Perkin-Elmer Corporation known in the field by the trademark Pyris 1™.

As is known, parent instrument 12 generally comprises a furnace 14 (FIG. 3) for heating specimen container. Furnace 14 is operatively connected to Pyris 1 software, and capable of heating up to temperatures of about 1000° C. or more. Furnace 14 comprises a conventional heating element 15 (FIG. 3) and is movable along a vertical axis between an upper and lower position. When in the uppermost position, glass top 16 seals against O-ring 18.

Figure 2:
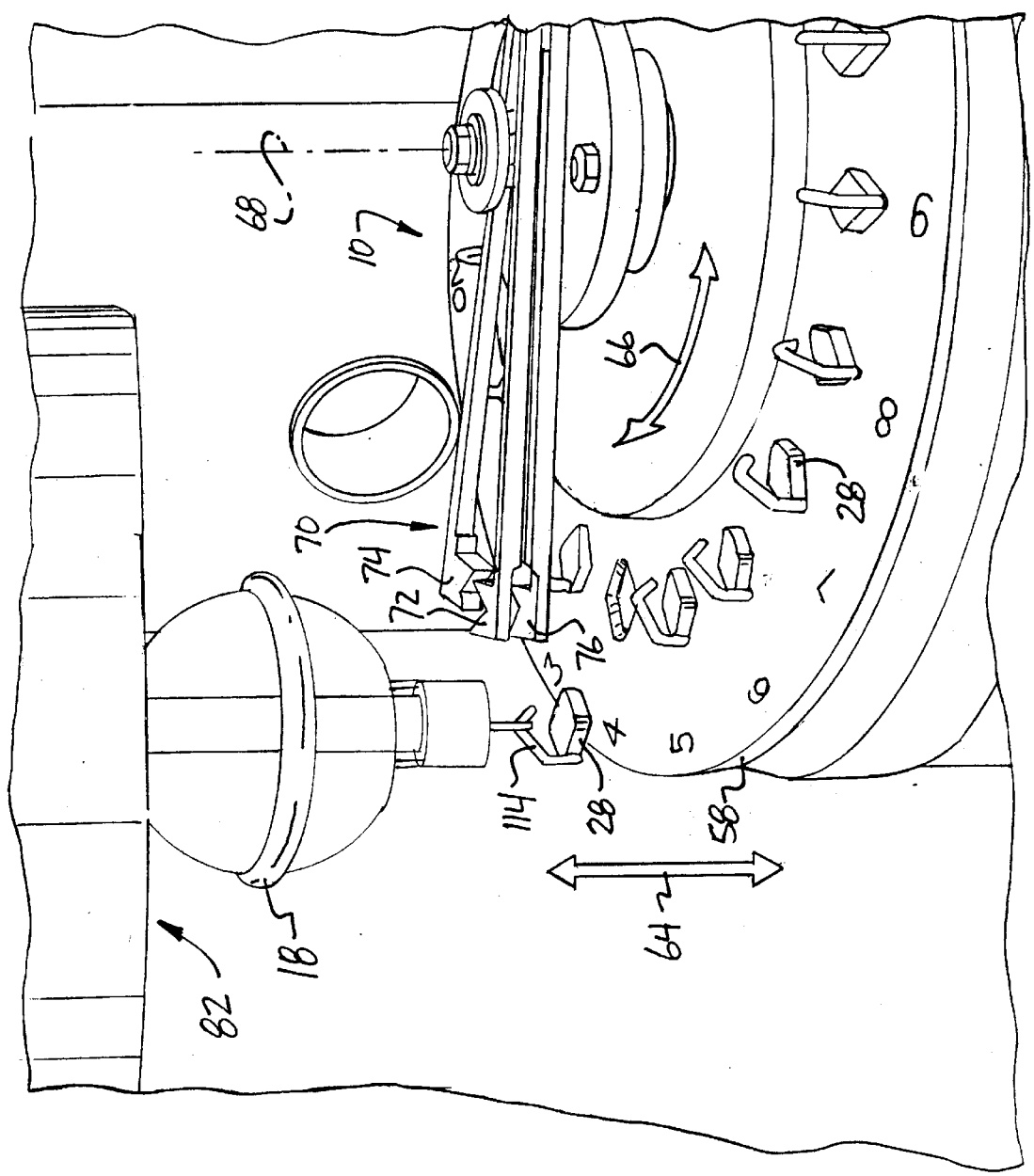
FIG. 2 is a side isometric view of the autosampler shown in FIG. 1, showing a crucible hanging from a hanging wire assembly and a gripping assembly in the open position.
Figure 4:
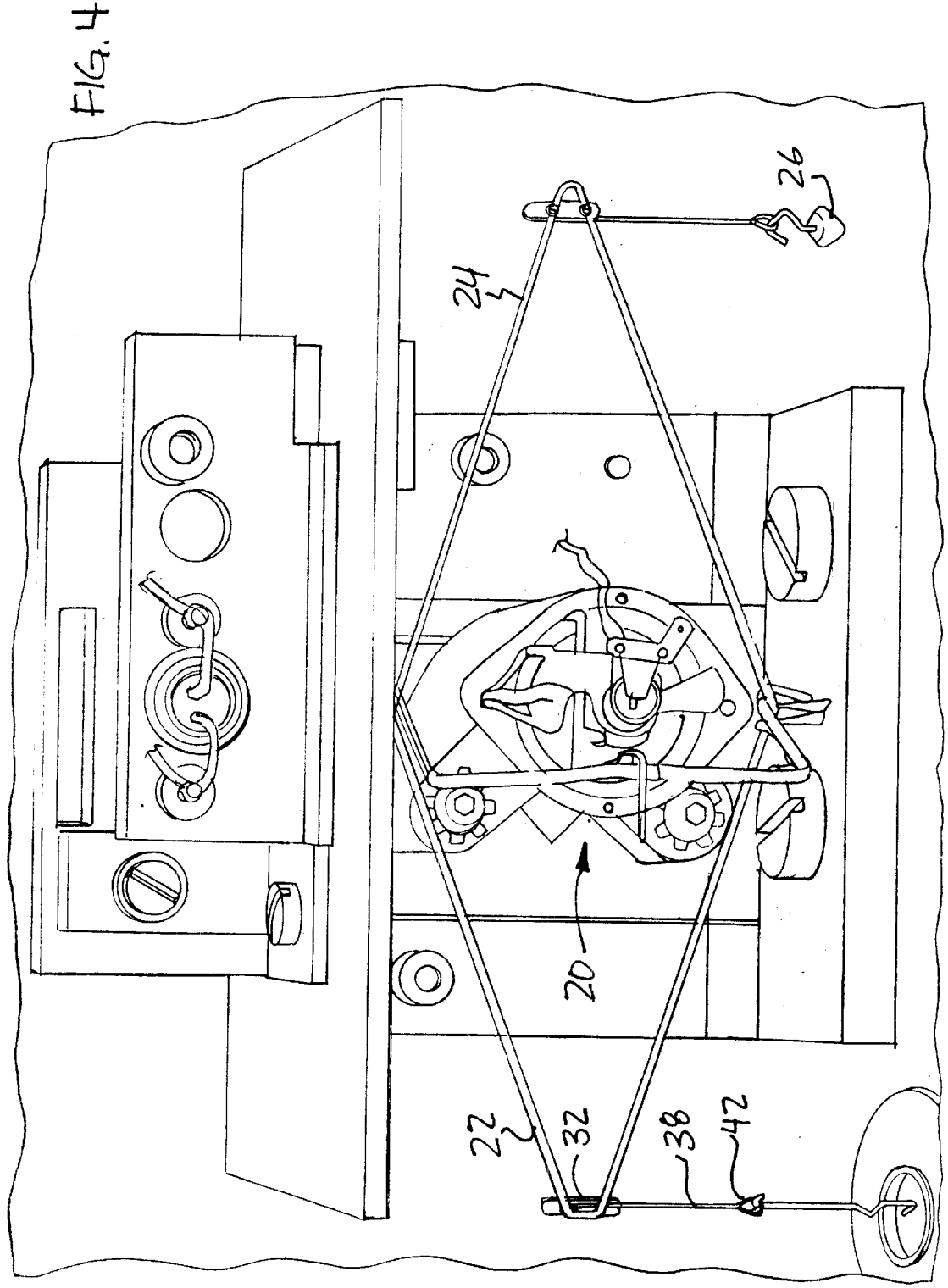
FIG. 4 is a side perspective view of the balance of the parent instrument, showing the hanging wire assembly on one end thereof.

As best shown in FIGS. 4 and 5, parent instrument 12 also comprises a conventional and extremely sensitive balance or weight measuring apparatus 20. Balance 20 has two arms 22, 24. A conventional tare weight 26 hangs from one arm 24. Arm 22 contains a series of wires or ribbons which serve to hold a specimen container 28 (FIG. 2).

More specifically, a glass sphere 30 is removably positioned on top of a hollow glass tube 32 and held in place by flange 34 and an adhesive 36, such as rubber cement, which is known in the art. A ribbon 38, preferably made of platinum, extends through the chamber of hollow glass tube 32 and is connected to sphere 30. Ribbon 38 is rotatable in the direction shown by arrow 40. Ribbon 38 has a loop 42 formed at one end thereof.

In conventional parent instruments, wire members which hold the specimen container during the analysis have been known to break. When the wire breaks or bends, it must be replaced. Disadvantageously, the sensitivity of the balance of prior art devices is typically damaged or destroyed during the replacement process. Advantageously, and unlike prior art instruments, the use of the removable adhesive 36 and flange 34 to position platinum ribbon 38 renders ribbon 38 easily replaceable. Further, when ribbon 38 is replaced, the sensitivity of balance 20 is not damaged or destroyed.

Crimped wire 46 having hook 44 is positioned in loop 42 of ribbon 38. Crimped wire 46 can be made of any suitable material but is preferably made of nichrome or quartz. Crimped wire 46 has two ends defining an axis 48 therebetween. Advantageously, crimped wire 46 has at least one point 50 which is displaced from axis 48, i.e. includes a bend. In the preferred embodiment, the angle formed by members 52, 54 at location 50 is about 90°. Crimped wire 46 has hook 56 formed at the end thereof for connecting specimen container 28 (FIG. 2) thereto.

Figure 3:
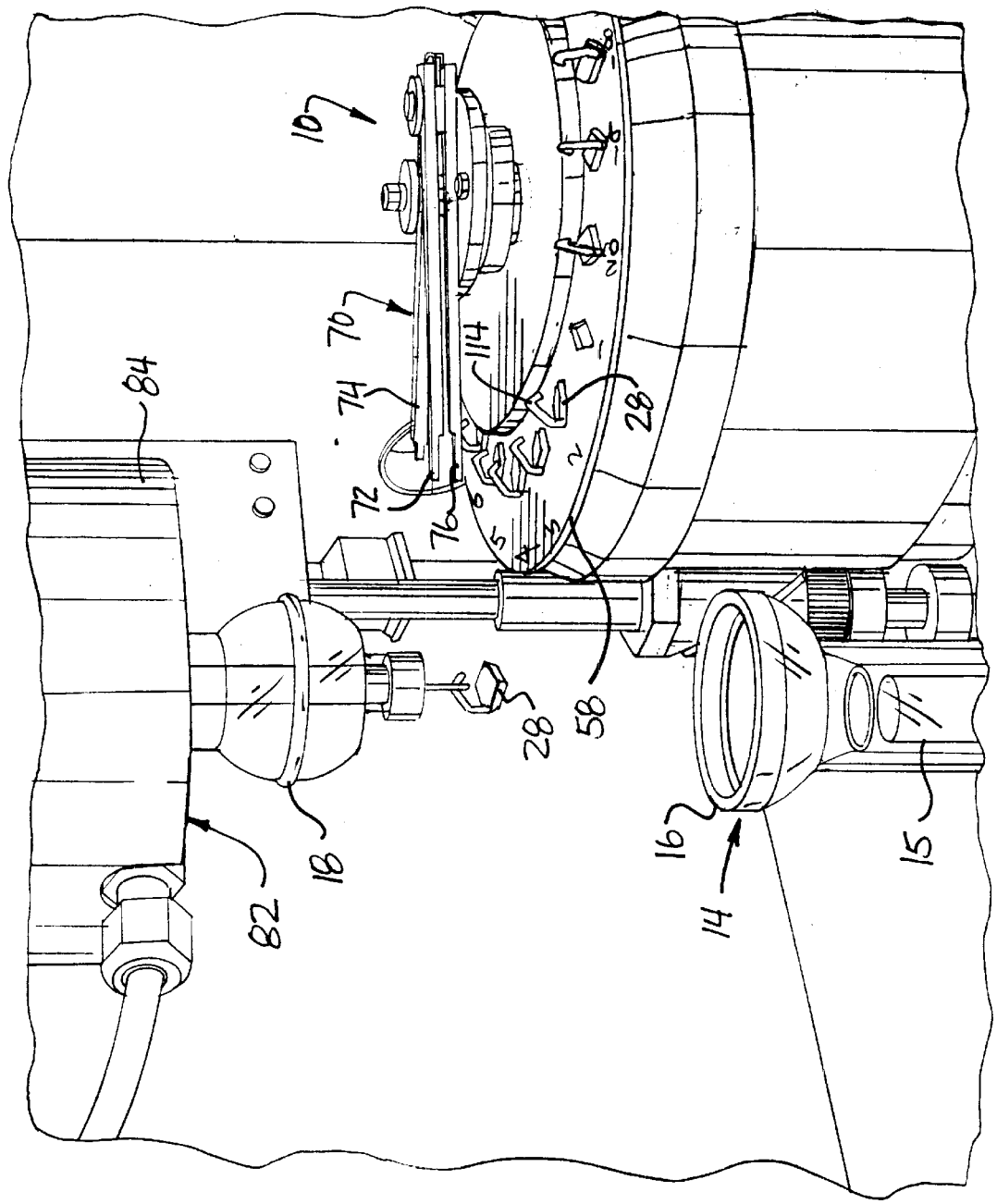
FIG. 3 is a side isometric view of the autosampler similar to the one shown in FIG. 2, wherein the autosampler has moved to a "mid" position.
Figure 11:
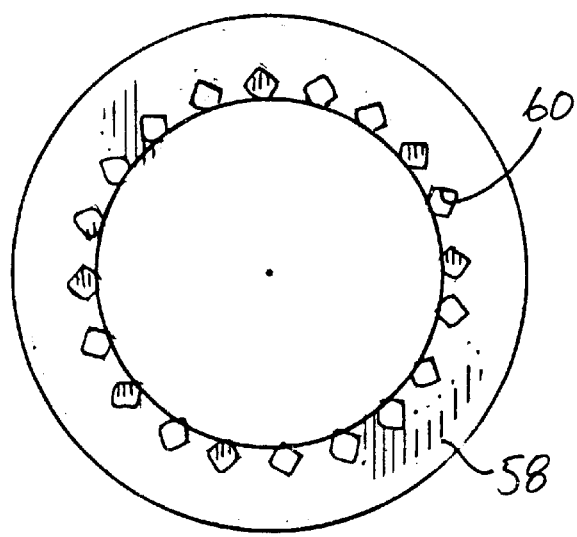
FIG. 11 is a top schematic view of a sample tray table shown in FIG. 1.

Referring in detail to FIGS. 1–3. autosampler 10 is removably fixed and operatively connected to parent instrument 12. Autosampler 10 comprises at least one specimen tray 58, also shown in FIGS. 11 and 12. Tray 58 has a plurality of recesses 60 for receiving specimen container 28 (FIG. 2). Preferably there are at least 20 recesses, but it should be understood that as many recesses could be formed as necessary.

Figure 12:
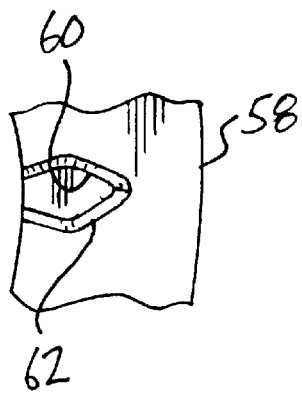
FIG. 12 is an enlarged and broken away view of a recess in the sample tray table shown in FIG. 11.

Each of the recesses is given a unique identifying number for easy sample identification. At least one, and preferably all, of the recesses 60 has at least one beveled edge 62 to facilitate placement of the specimen container 28 therein (FIG. 12). Also, it is preferable that each recess 60 be uniquely shaped so that the specimen container 28 is always properly positioned and oriented therein. Still further, it is preferred that at least one of the recesses of the specimen tray be substantially rounded to facilitate placement of the specimen container 28 therein.

Figure 14:
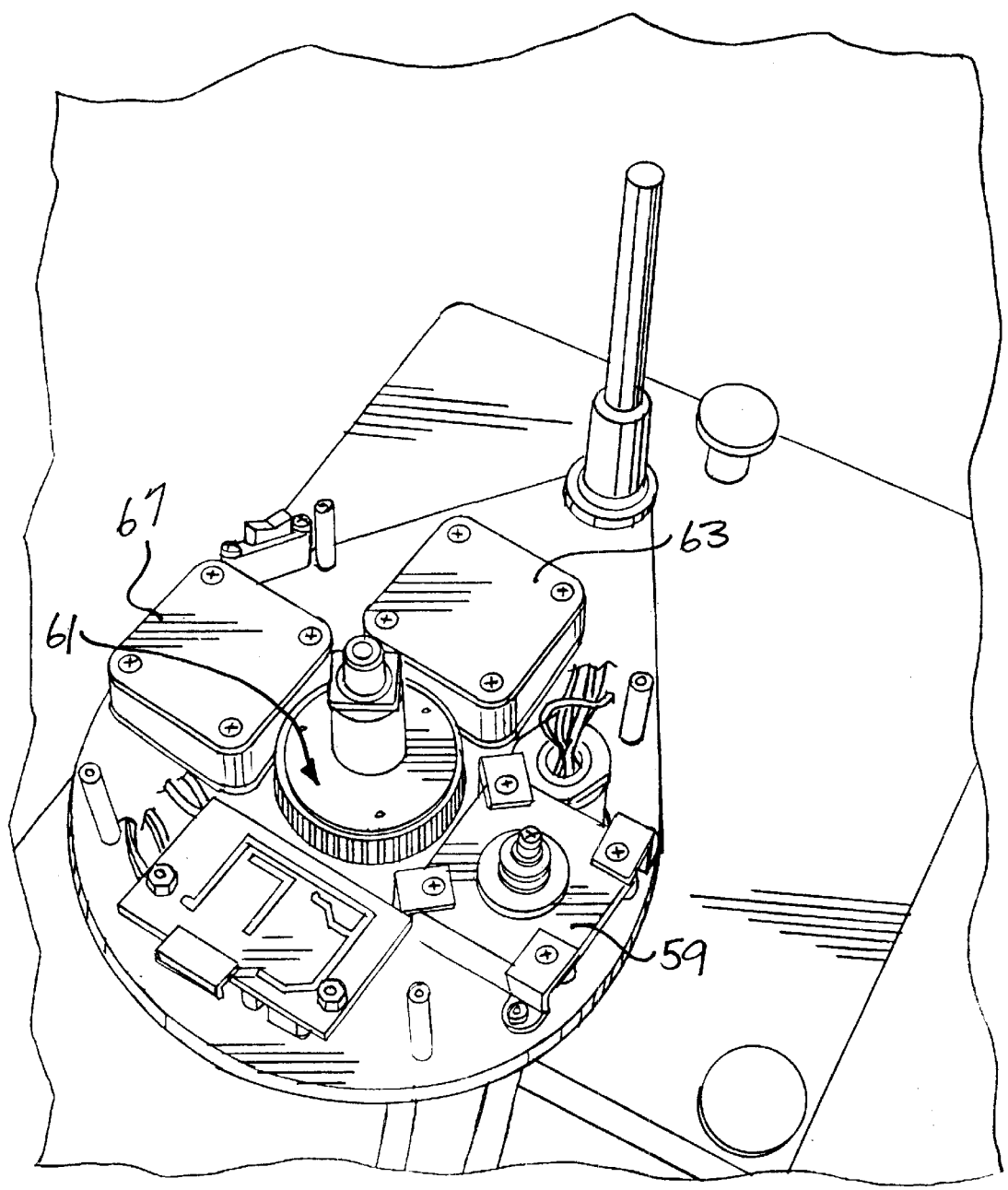
FIG. 14 is a top view of the autosampler shown in FIG. 1 with the cover removed for clarity.

Specimen tray 58 is movable via a conventional stepper motor 59 and a slip clutch and electromagnetic brake assembly 61 between an upper and lower position as indicated by arrow 64 and rotatable in the direction shown by arrow 66 about a central axis 68 (see FIGS. 2 and 14). Any suitable stepper motor known in the art may be used. In the embodiment, a stepper motor having the following operational characteristics is preferred: 12 volts DC; 0.3 amps; 2 phase; and 0.9 mm/step.

A second stepper motor 63 (FIG. 14) swings autosampler 10 toward (FIGS. 1 and 2) and away from (FIG. 3) the specimen load position. This stepper motor may have the following operational characteristics: 12 volts DC; 0.3 amps; 2 phase; and 0.9 mm/step. Autosampler 10 is attached to the parent instrument 12 via a pivot shaft 65 (FIG. 1). Autosampler 10 is movable between a loading and an unloading position and, when not loading or unloading, autosampler 10 moves to a "safe" location, i.e., away from the load position, where the specimen is analyzed.

Movement by these two motors, together with a gripper motor 67 (discussed below), allows gripping assembly 70 (discussed in detail below) to access each container 28, transfer it from the specimen tray 58 and attach it to hook 56 of crimped wire 54, and return it to its appropriate position on the sample tray 58 after the analysis is completed. It should be understood, however, that any suitable means known in the art may be used to move autosampler 10, such as mechanical, hydraulic or magnetic means, or combinations thereof.

Referring to FIGS. 2, 3, 6, 6A and 6B, autosampler 10 further comprises a gripper assembly 70 operatively connected to specimen tray 58 and movable between an open position (shown in FIGS. 2, 3 and 6B) and a closed position (FIGS. 6 and 6A). When gripper assembly 70 is in the closed position, it grips crimped wire 46 about the point 50 (FIG. 5) at which it is displaced from its linear axis, and stabilizes it while the specimen tray 58 moves so as to connect the specimen container 28 to the crimped wire 46.

More specifically, gripper assembly 70 comprises upper, middle and lower gripping fingers 72, 74, 76, respectively (each finger may not be shown in all the drawings). Each finger 72, 74, 76 may be made of any suitable material, however, they are preferably made of aluminum.

In one embodiment, the upper 72 and lower 76 gripping finger are substantially identical in design. Each gripping finger has two ends with a substantially V-shaped portion 80 cut therefrom for receiving crimped wire 46 therein.

Middle gripping finger 74 is positioned between the upper and lower fingers 72, 76, respectively, and, as best shown in FIGS. 2, 6 and 6B, opposes fingers 72, 76. Middle finger 74 has two ends and a portion 78 at one end thereof sized and shaped to receive crimped wire 46 at the point 50 where crimped wire 46 is maximally displaced from its axis 48. As shown in FIG. 6A, when in the closed position, middle gripping finger 74 cooperates with the upper and lower gripping finger 72, 76, to grip and stabilize crimped wire 46 so that specimen container 28 may be positioned on hook 56.

Middle gripping finger 74 is designed to push against crimped wire 46 at the location of the angle formed by members 52, 54. It should be understood that any suitable size angle could be formed by members 54, 56 and any suitable cutout portion of finger 74 could be used so long as middle finger 74 cooperates with fingers 72, 76 to stabilize crimped wire 46 while specimen container 28 is loaded and unloaded.

Gripping fingers 72, 74, 76 are biased to a closed position. Fingers 72, 74, 76 may use any suitable means to move between an open and closed position, such as hydraulic, mechanical and magnetic means and/or combinations thereof. In one embodiment, a motor 67 (FIG. 14) turns a cam (not shown) which simultaneously activates the fingers. Although any suitable conventional motor may be used, in one embodiment, a motor having the following operational characteristics is used: 12 volts DC; 0.3 amps; 2 phase; and 0.9 mm/step.

As discussed above, static build up generally occurs on the surface of the glassware surrounding the TGA furnace 14, and is aggravated by movement of the glassware 16 over insulating material, such as O-ring 18. The resulting electrostatic fields negatively influence the readings of the highly sensitive microbalance 20 of the parent instrument 12 because the sample container 28 is moved off-center due to its attraction to the surface of the glassware. Advantageously, parent instrument 12 comprises an electrostatic discharge device 82, which is best shown in FIGS. 3, 7, 8 and 9, which substantially reduces and/or eliminates the electrostatic fields described above.

Electrostatic discharge device 82 comprises a housing 84 which is operatively and removably attached to parent instrument 12, and is most preferably mounted above the TGA furnace 14. The housing 84 surrounds the uppermost portion of the furnace assembly 14 and is therefore in close proximity to the region of static buildup.

Figure 7:
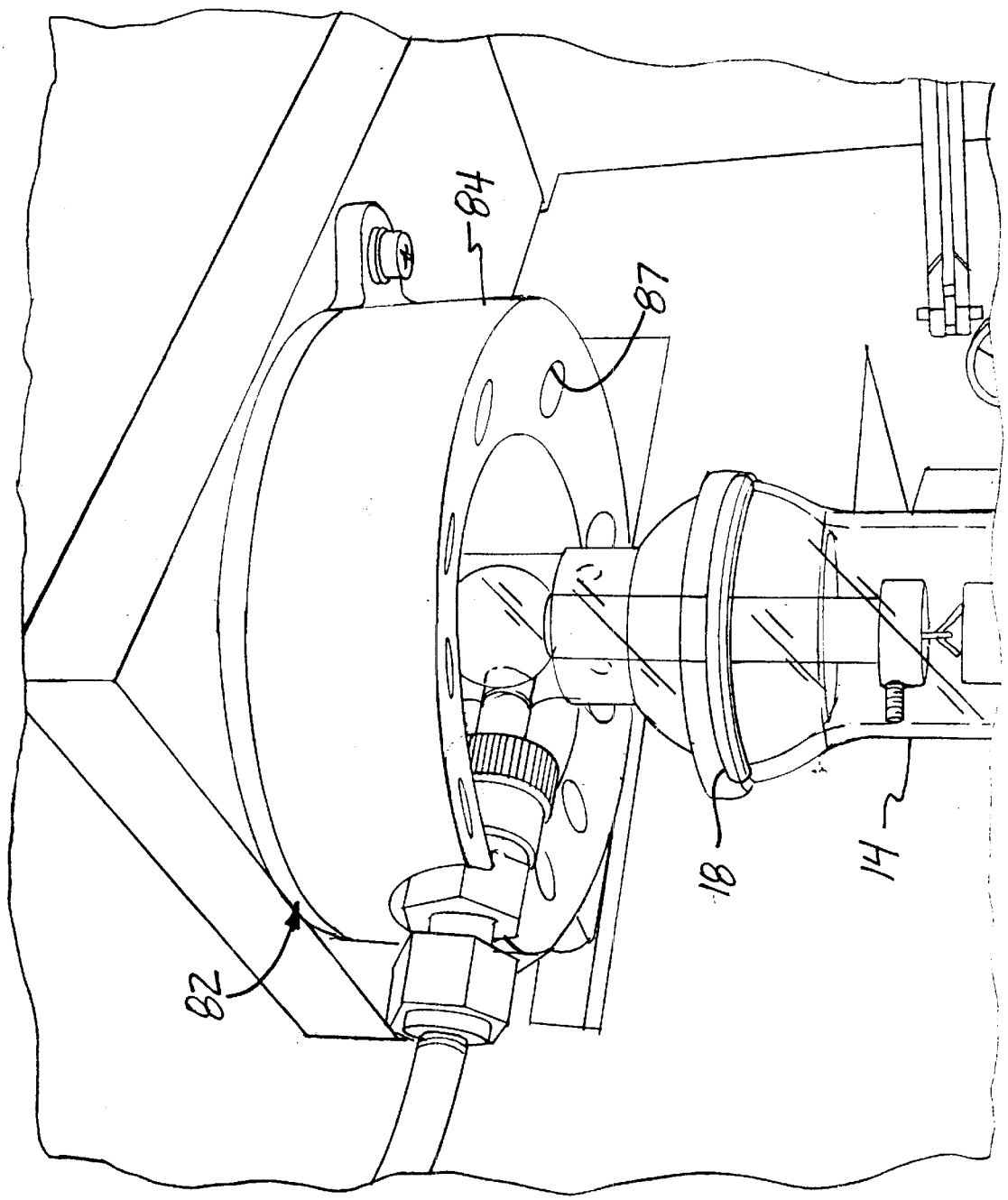
FIG. 7 is a bottom perspective view of an electrostatic discharge device constructed in accordance with the present invention.
Figures 8, 9:
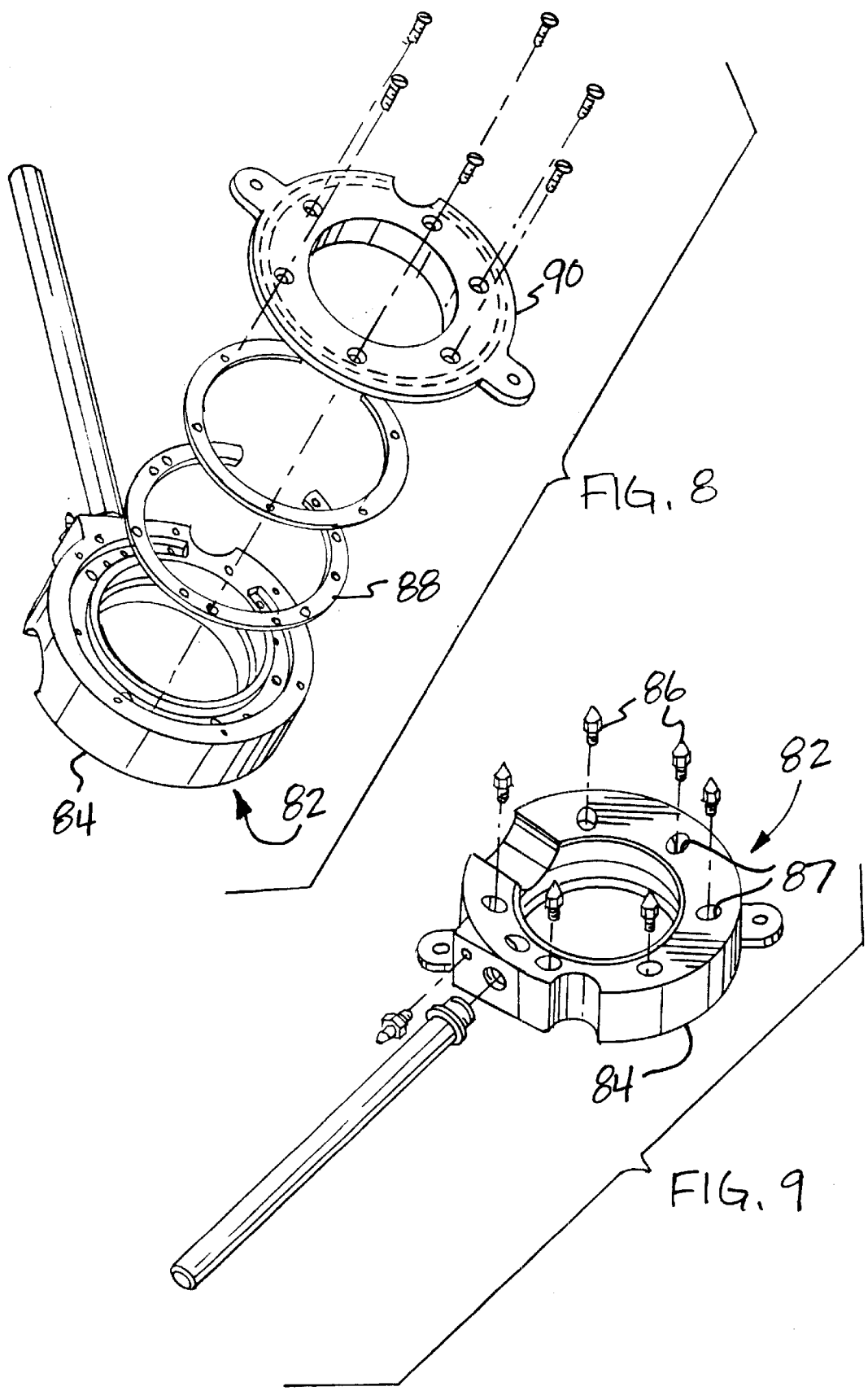
FIG. 8 is an exploded view of the top of the electrostatic discharge device shown in FIG. 7.
FIG. 9 is an exploded view of the bottom of the electrostatic discharge device shown in FIG. 7.

Discharge device 82 comprises at least one, and preferably a plurality of, substantially sharp objects 86, such as heavy-duty metal pins (see FIG. 9). Each of the pins 86 are substantially equidistantly positioned about a metallic ring 88 through a circular cavity 87 (FIG. 7). Each cavity 87 is sufficiently deep so that the pins 86 are not directly exposed to the touch and the walls of each cavity 87 are angled to direct the ions toward the electrostatic field. As the pinpoints wear due to normal use over extended periods of time, the production of ions at each point may diminish. Advantageously, each pin 86 may be easily replaced to restore full production of ions.

A voltage source is electrically connected to each pin 86 for supplying voltage to the pin 86 and generating multiple free ions as a result thereof. Any suitable voltage amount may be used: in the most preferred embodiment about 5,000–6,000 VAC is used (see FIG. 10).

Referring again to FIGS. 8 and 9, above the metallic ring 88 is a gas plenum 90 that feeds a low-pressure gas stream from a gas source 94 into each cavity 87 which is in fluid communication therewith. Preferably, compressed air or nitrogen is used. The gas stream causes the positive and negative free ions generated at the pinpoints 86 to be propelled downward toward the furnace 14. The combined flow from each cavity 87 (FIG. 7) effectively blankets the furnace area 14 with free ions that neutralize electrostatic fields on the glassware above and below O-ring 18, i.e., the top half of the furnace, and on the surface of the autosampler tray 58 and gripper assembly 70.

A schematic diagram of the electrostatic discharge device 82 is shown in FIG. 10. The low-pressure gas source 94 is connected from within the analytical instrument 12 to the gas plenum within the housing 84 through a port in the housing 84. Any suitable, standard flexible tubing and fittings may be employed to connect the gas source 94 to the housing 84. A second port connects the high voltage, alternating current source 98 to the metallic ring 88 within housing 84 via resistive element 99. The second port is comprised of a long insulating tube 96 that extends into the discharge device 82. Conventional resistive element 99, nominally about eight megohms, is housed inside tube 96 and limits electrical current flow into the pinpoint 86 should a short circuit occur or in the event that the operator of the TGA 12 comes into contact with any of the metallic elements of device 82. Conventional high voltage AC transformer 98, housed inside the parent instrument 12, is advantageously designed to limit self-generation of ions within its own environment.

Activation of both the low-pressure gas source 94 and the high voltage transformer 98 are controlled by a microprocessor 100, electrically and operatively connected to interface electronics 102 housed inside the parent instrument 12. Discharge device 82 may be activated manually or automatically by entering the appropriate command into the Pyris 1 software from the keyboard of the host computer. Preferably, the gas and high voltage supplies 94, 98, respectively, are turned on immediately prior to the separation of the upper and lower halves of the furnace 14. While the furnace 14 is separated, the ionization device 82 remains on so that components of the furnace 14 and the sample handling area are flooded with ions.

Advantageously, the discharge device 82 is designed so that it automatically stops operating if the furnace 14 remains open (as shown in FIG. 3) for a long period of time, such as greater than three minutes. This reduces the amount of ozone produced by the discharge device 82 and reduces the operator's exposure to the high voltage within the housing assembly 84.

When the furnace assembly 14 is commanded to close, the ionization device remains on, or turns on again as the case may be. The time to close the furnace 14 is programmable, thereby allowing adequate time to discharge lingering electrostatic fields. All timing related changes are made by modifying the control firmware (not shown) within the microprocessor 100.

Figure 13:
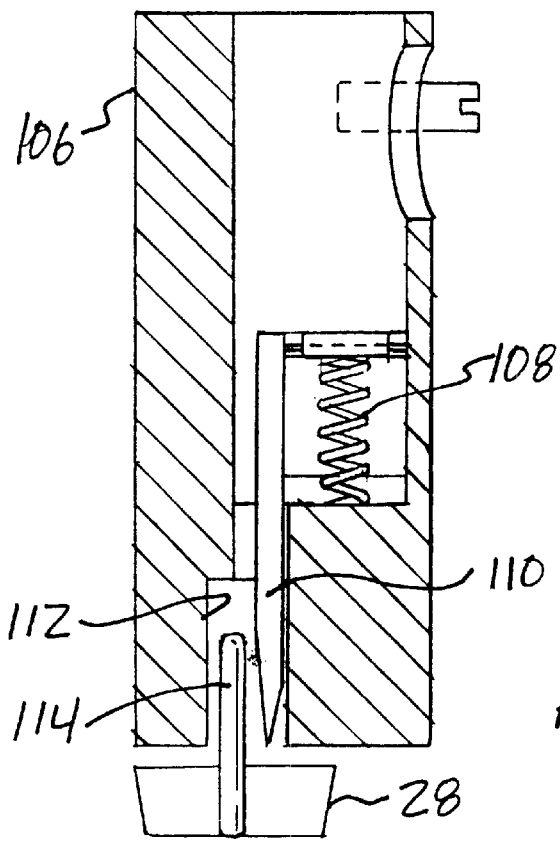
FIG. 13 is a cross-sectional view of a puncture device which is operatively connected to the autosampler shown in FIG. 1, constructed in accordance with the present invention.

Parent instrument 12 also comprises an apparatus 104 for puncturing holes into the top of a sealed specimen container 28, which is best shown in FIG. 13. Puncturing apparatus 104 comprises a housing 106, operatively connected to parent instrument 12, and uses the autosampler's sample tray 58 up/down movement to move to and from a puncture position (FIG. 13) and a rest position (not shown); that is, puncturing apparatus 104 is movable via the sample tray 58 between an upper and lower position. Steel spring 108 biases housing 106 into the lower position. It should be understood that any suitable means may be used to bias housing 106 into the lower position.

A sharp or pointed object 110, such as a pin, is housed inside the puncturing device housing 106 for puncturing a hole into the top of a sealed specimen container 28. Any suitable strong, sharp object may be used. In the preferred embodiment, a steel pin is used.

A slot 112 is formed at the bottom of the housing 106 and is sized and shaped to receive a hook or handle 114 (FIGS. 2, 3 and 13) of specimen container 28.

In operation, when the specimen tray 58 (FIGS. 1–3 and 11) moves into the upper position, the sealed specimen container 28 forces the housing 106 to move from the lower position to the upper position thereby exposing pin 110 and causing it to puncture the top of the sealed specimen container 28.

A method for handling and transferring specimen containers 28 generally follows the operation of autosampler 10 discussed above and comprises the following steps. First, an operator programs autosampler 10 and loads specimen containers 28 containing specimens onto specimen tray 58.

Gripper 70 begins each session in the open position and tray 58 is in the lowermost position and in a "safe" position, which is farthest from furnace 14. Autosampler 10 is then instructed by the operator via software to begin a session, i.e., to pick-up a particular sample container 28 and to load it into furnace 14.

Autosampler 10 swings via stepper motor 63 from the "safe" position to a "mid" position, which is between the "safe" position and the "loading" position. At the "mid" position, tray 58 rotates via stepper motor 59 to the desire sample position, which positions the predetermined container 28 immediately to the left of hook 56 of crimped wire 46.

Autosampler 10 then swings until it is in a "loading" position, a position in which it is directly over the lowered furnace 14. Gripping fingers 72, 74, 76 then close via stepper motor 67 around crimped wire 46 and stabilize and align it. Tray table 58 then raises up, rotates counterclockwise to deposit the hook or handle 114 of container 28 onto hook 56 (see FIGS. 2 and 3). After the container 28 is properly positioned on crimped wire 46, the tray table 58 lowers to its lowermost position via stepper motor 59 and gripping fingers 72, 74, 76 move via stepper motor 67 to their normally open position. Then, autosampler 10 swings to its "mid" position where the host computer conducts a quick safety check and then autosampler 10 swings to the "safe" position via stepper motor 63.

Next, furnace 14 moves from its lowermost position to the upper position and encloses specimen container 14 therein by forming a tight seal at O-ring 18. Then, the furnace is activated, the temperature inside the furnace rises to the pre-selected temperature, and the desired thermogravametric analysis takes place. The weight differential is measured by balance 20 and pertinent data is recorded by the host computer.

After the appropriate test has been completed, the furnace 14 cools down and moves to its lowermost position. Autosampler 10 then prepares to unload the specimen container 20 from the furnace 14. First, autosampler 10 swings from its "safe" position to the "mid" position. Tray table 58 rotates via stepper motor 59 until the recess for receiving container 28 is just to the right of specimen container 28 as it hangs on wire 46, and autosampler 10 rotates to the "load" position. Gripper fingers 72, 74, 76 then close via stepper motor 67 around wire 46 and stabilize it. Tray 58 then moves via stepper motor 59 to its uppermost position. Table 58 then rotates via stepper motor 59 clockwise and picks up sample container 28. Table 58 then moves to its lowermost position and gripping fingers 72, 74, 76 open via motor 67 and remain in the normally open position. Autosampler 10 then swings to its "mid" position where a quick safety check is conducted and then swings again to its "safe" position via motor 63.

If specimen container 28 is sealed, its top must be punctured prior to its being placed in furnace 14. Puncturing device 104 (FIGS. 1 and 13) punctures a hole in the top of sealed container 28 when instructed by an operator via instructions entered into the host computer. Puncturing device 104 operates in the manner discussed above.

After autosampler 10 has been properly programmed and loaded, it advantageously operates without further human operator assistance. Further, the autosampler 10 has the ability with the Pyris 1™ program, when properly programmed, to abort an analysis if problems occur with the transfer of a specimen container 28 and to generate an error message which is displayed on the display screen of the host computer (not shown).

In its most preferred embodiment, autosampler 10 is capable of loading up to 20 samples without operator assistance, thus, freeing the operator to perform other tasks. Advantageously, because of the safety features built into the autosampler 10, the operator does not need to be in the vicinity of the autosampler 10 while it is working. Thus, the operator may load autosampler 10 near the end of the work day, and upon returning to work the next day, find the results of the analysis. As a result, autosampler 10 saves the operator much time and energy.

It should be understood that the foregoing is illustrative and not limiting and that obvious modifications may be made by those skilled in the art without departing from the spirit of the invention. Accordingly, reference should be made primarily to the accompanying claims, rather than the foregoing specification, to determine the scope of the invention.

What is claimed is:

1. An apparatus for manipulating a specimen container comprising:
   a parent instrument comprising a crimped wire having two ends defining an axis therebetween, the crimped wire having at least one point which is displaced from the axis;
   an autosampler, operatively connected to the parent instrument, comprising:
     a gripper assembly movable between an open and a closed position;
     at least one specimen tray positioned about the gripper assembly and having a plurality of recesses therein for receiving at least one specimen container, the specimen tray movable between an upper and a lower position and rotatable about a central axis; and
     wherein when the gripper assembly is in the closed position it grips the crimped wire about the point at which it is displaced from the axis and stabilizes it while the specimen tray moves so as to attach the specimen container to the crimped wire.

2. The apparatus of claim 1 wherein the gripper assembly further comprises:
   an upper and a lower gripping finger, each finger having two ends, each finger having one end with a substantially V-shaped portion for receiving the crimped wire therein; and
   a middle gripping finger having two ends, the middle gripping finger positioned between and opposed to the upper and lower gripping finger and having a portion at one end thereof sized and shaped to receive the crimped wire at the point where the crimped wire is displaced from its axis; and
   wherein the middle gripping finger cooperates with the upper and lower gripping fingers to grip and stabilize the crimped wire.

3. The apparatus of claim 1, wherein at least one of the recesses of the specimen tray has at least one beveled edge to facilitate placement of the specimen container.

4. The apparatus of claim 1, wherein at least one of the recesses of the specimen tray is shaped so that the specimen container is positioned therein.

5. The apparatus of claim 4, wherein at least one of the recesses of the specimen tray is substantially rounded.

6. The apparatus of claim 1 further comprising an apparatus for puncturing a hole into the specimen container, the puncturing apparatus comprising:

a housing operatively connected to the parent instrument, the housing movable between an upper and lower position and biased toward the lower position;

a pointed object housed inside the housing; and wherein when the specimen tray moves into the upper position, the specimen tray moves a specimen container positioned in one of the recesses of the specimen tray and under the pointed object upward forcing the housing to move from the lower position to the upper position thereby exposing the pointed object and causing it to puncture the specimen container.

7. The apparatus of claim 6 wherein the puncturing apparatus further comprises a spring, housed inside the housing, for biasing the housing toward the lower position.

8. The apparatus of claim 7 wherein the puncturing apparatus housing includes a slot therein, the slot sized and shaped to receive a hook of the specimen container.

9. The apparatus of claim 1 further comprising an electrostatic discharge device comprising:

an electrostatic discharge device housing attached to the parent instrument, the electrostatic discharge device housing having a channel thereabout;

at least one substantially sharp object positioned inside the electrostatic discharge device housing and in fluid communication with the channel;

a voltage source, electrically connected to the at least one substantially sharp object for supplying voltage thereto and generating multiple free ions as a result thereof;

a source of pressurized gas for generating a gas stream, the pressurized gas source operatively connected to the electrostatic discharge device housing and in fluid communication with the channel, for forcing gas through the channel and around the at least one substantially sharp object; and wherein the gas stream directs the free ions toward an electrostatic field to neutralize ions therein.

10. The apparatus of claim 9 wherein the at least one substantially sharp object comprises about seven substantially sharp objects substantially equidistantly spaced about the channel.

11. The apparatus of claim 9 wherein the voltage source supplies about 5,000 volts of alternating current.

12. The apparatus of claim 9 wherein the gas comprises air.

13. The apparatus of claim 9 wherein the gas comprises nitrogen.

* * * * *